United States Patent
Lee

(10) Patent No.: US 8,460,381 B2
(45) Date of Patent: Jun. 11, 2013

(54) METHODS AND DEVICES FOR THE TREATMENT OF INTERVERTEBRAL DISCS DISORDERS

(75) Inventor: Elaine Lee, Santa Clara, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 120 days.

(21) Appl. No.: 13/076,645

(22) Filed: Mar. 31, 2011

(65) Prior Publication Data
US 2012/0253466 A1    Oct. 4, 2012

(51) Int. Cl.
A61F 2/44 (2006.01)
(52) U.S. Cl.
USPC ........................................................ 623/17.11
(58) Field of Classification Search
USPC 623/17.11, 17.16, 23.57, 23.6; 424/422–426, 424/94.1, 94.6, 94.61, 94.62, 489
See application file for complete search history.

(56) References Cited

U.S. PATENT DOCUMENTS

| | | | |
|---|---|---|---|
| 4,696,816 A * | 9/1987 | Brown | 424/94.65 |
| 7,163,545 B2 | 1/2007 | Yaszemski et al. | |
| 7,169,405 B2 * | 1/2007 | Trieu | 424/426 |
| 2001/0020188 A1 | 9/2001 | Sander | |
| 2002/0106362 A1 | 8/2002 | Masuda et al. | |
| 2004/0033221 A1 | 2/2004 | Masuda et al. | |
| 2007/0116697 A1 | 5/2007 | Osterhout et al. | |
| 2007/0128575 A1 * | 6/2007 | Trieu | 433/25 |
| 2007/0250044 A1 | 10/2007 | Trieu | |
| 2011/0052711 A1 | 3/2011 | Wang et al. | |

OTHER PUBLICATIONS

International Search Report and Written Opinion for PCT/US2012/024810 the counterpart application, mailed on Sep. 19, 2012.

* cited by examiner

*Primary Examiner* — Pedro Philogene
(74) *Attorney, Agent, or Firm* — Sorell Lenna & Schmidt LLP

(57) ABSTRACT

Devices for the treatment of intervertebral discs are described. The devices, when implanted into the nucleus pulposus of an intervertebral disc, are specifically configured with an inert outer layer and an inner layer containing at least one chemonucleolysis agent so as to provide a delayed and controlled release of the chemonucleolysis agent from the inner layer into the disc. The implant can be an elongated solid body having a tapered or rounded insertion end having at least one therapeutic agent in the inner layer of the implant surrounded by an outer layer of inert material.

21 Claims, 2 Drawing Sheets

METHODS AND DEVICES FOR THE TREATMENT OF INTERVERTEBRAL DISCS DISORDERS

TECHNICAL FIELD

The present application relates generally to methods and devices for the treatment of intervertebral discs and, in particular, to delayed release devices comprising a chemonucleolysis agent or multiple active agents and to methods of treatment comprising implanting the devices into an intervertebral disc.

BACKGROUND

The intervertebral discs are cartilaginous plates surrounded by a fibrous ring that lie between the vertebral bodies and serve to cushion them. Through degeneration, wear and tear, and trauma, the fibrous tissue (annulus fibrosus) constraining the soft disc material (nucleus pulposus) may tear or become compressed. This squeezing or protrusion of the disc has been called herniated disc, ruptured disc, herniated nucleus pulposus, or prolapsed disc. The extruded nucleus pulposus may press on a spinal nerve, which may result in nerve damage, pain, numbness, muscle weakness and even paralysis.

Common methods of providing relief for damaged intervertebral discs include surgical removal of all or a portion of the intervertebral disc followed by fusion of the adjacent vertebrae. Although fusion can eliminate certain of the aforementioned symptoms, the restricted motion of the fused segment increases the range of motion required of the adjoining intervertebral discs and can therefore enhance their degeneration. As an alternative to fusion, the disc can be replaced with a spacer designed to simulate healthy intervertebral disc motion. The materials from which these disc spacers are made (e.g., polymeric and metallic materials), however, may disintegrate in the body or break down under repeated stress over prolonged periods.

Treating by intradiscal injecting of a material that can dehydrate the nucleus and thereby reduce pressure can be effective if injected in the correct location. However, healthy tissue can be damaged in the event that the injection is not in the correct location. Accordingly, there still exists a need for improved devices and methods for the treatment of intervertebral discs.

SUMMARY OF THE INVENTION

Implants and methods are provided herein for treating conditions associated with disorders of an intervertebral disc in a patient. The implants and treatments of the present invention include tracking the implant for proper placement prior to release of active chemonucleolysis agents.

According to one embodiment of the present invention an intervertebral disc implant comprises an inner layer having at least one chemonucleolysis agent encapsulated by an inert outer layer is provided. The inert outer layer is configured so as to fully encapsulate the inner layer. Upon placement of the implant of the present invention into the nucleus pulposus of a diseased intervertebral disc, the inert outer layer does not immediately degrade and therefore does not immediately release the chemonucleolysis agent contained in the inner layer into tissue surrounding the implant. That is, until the inert outer layer is bioeroded, the chemonucleolysis agent of the inner layer remains within the implant. This allows the surgeon time to make sure that the implant is positioned correctly before the chemonucleolysis agent is released into the surrounding tissue. This prevents unwanted tissue damage caused by proteolytic degradation of healthy tissue by the chemonucleolysis agent when the implant is placed in an incorrect location.

In one embodiment of the present invention, the inert outer layer comprises a traceable marker, such as an x-ray or radio-opaque marker that is used to confirm the proper location of the implant after implantation and prior to the release of chemonucleolysis agent from the inner layer. If it is determined that the implant is not in the desired location, the implant can be removed prior to the inert outer layer being compromised and therefore no chemonucleolysis agent is released. Once the misplaced implant is removed, the implant can be repositioned and the new location confirmed. When the implant is in the desired location, the inert outer layer of the implant will begin to dissolve and/or degrade over time, and the chemonucleolysis agent is released into the tissue surrounding the implant.

In another embodiment of the present invention, the intervertebral disc implant of the present invention is coated with a coating that is disposed on the outer layer of the implant. Once the coating is dissolved and/or degraded, the inert outer layer begins to dissolve and/or degrade and the chemonucleolysis agent is released from the inner layer into the tissue surrounding the implant. This coating provides an additional barrier to immediate release of the chemonucleolysis agent from the inner layer therein providing additional time for the surgeon to determine whether the implant is in the desired location. The coating can contain traceable markers such as x-ray markers or other tracking markers that can be used to determine the position of the implant. The coating can provide lubricity for ease of delivery. The coating can provide enhanced friction for reducing undesired migration of the implant.

In another embodiment of the present invention, a method for treating at least one condition of an intervertebral disc in a patient in need of such treatment and tracking the implant for proper placement is provided. The method comprises (a) placing the intervertebral disc implant of the present invention comprising markers for tracking the position of the intervertebral disc implant into an intervertebral space of a patient. Once placed in the patient, (b) the location of the intervertebral disc implant is determined by detecting the location of the marker (i.e., using x-ray imaging to detect x-ray marker), and if the implant is not in the correct location the surgeon proceeds to step (c) recited below. If it is determined that the implant is in the correct location, step (c) can be skipped and the surgeon proceeds to step (d). Step (c) includes removing the intervertebral disc implant from the incorrect location and placing the implant into a location different than where it was removed. Once this is done step (b) is repeated in order to determine whether the new position of the intervertebral disc implant is correct. If the implant is in the correct position, the surgeon then moves on to step (d); if not, step (c) is repeated. In step (d) the intervertebral disc implant remains in position so that the inert outer layer can bioerode and the chemonucleolysis agent is released from the inner layer into the surrounding tissue. Once released, the chemonucleolysis agent is allowed to proteolytically degrade the nucleus pulposus thereby treating the condition.

In another embodiment of the present invention, additional therapeutic agents can be added to the inner layer and released with the chemonucleolysis agent. These agents include pain medication, growth factors, anti-inflammation agents, anti-infectious agents, as well as other active agents that can used to treat diseased intervertebral disc.

More details of these embodiments and others of the present invention are described in greater details in the sections below.

BRIEF DESCRIPTION OF THE DRAWINGS

The present disclosure will become more readily apparent from the specific description accompanied by the following drawings, in which.

DETAILED DESCRIPTION OF THE INVENTION

Figure 1:
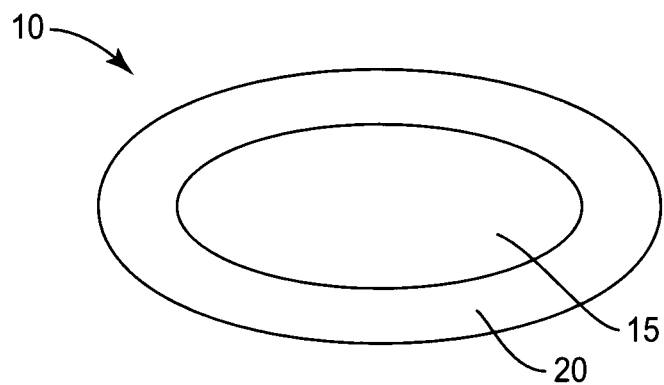
FIG. 1 shows a cross-section of an implant of the present invention.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

The headings in this application are not meant to limit the disclosure in any way; embodiments under any one heading may be used in conjunction with embodiments under any other heading.

It is noted that, as used in this specification and the appended claims, the singular forms "a," "an," and "the," include plural referents unless expressly and unequivocally limited to one referent. Thus, for example, reference to "an intervertebral disc implant" includes one, two, three or more intervertebral disc implants.

The term "practitioner" or "user" means a person who is using the methods and/or devices of the current disclosure on the patient. This term includes, without limitation, doctors (e.g., surgeons, interventional specialists, physicians), nurses, nurse practitioners, other medical personnel, clinicians, dentists, veterinarians, or scientists.

The term "therapeutic agent" may be used interchangeably herein with the terms "drug," "therapeutically effective amount," and "active pharmaceutical ingredient" or "chemonucleolysis agent." It will be understood that unless otherwise specified a "therapeutic agent" formulation may include more than one therapeutic agent, wherein exemplary combinations of therapeutic agents include a combination of two or more drugs.

A "therapeutically effective amount" or "effective amount" is such that when administered, the drug results in alteration of the biological activity, such as, for example, inhibition of inflammation, reduction or alleviation of swelling or inflammation in or near the nucleus pulposus of a diseased intervertebral disc etc.

The term "biodegradable" includes that all or parts of the implant will degrade over time by the action of enzymes, by hydrolytic action and/or by other similar mechanisms in the nucleus pulposus of the intervertebral disc. In various embodiments, "biodegradable" includes that the implant or part of the implant (e.g., microparticle, microsphere, etc. incorporated into the inner or outer layer of the implant) can break down or degrade within the area of implant (i.e. in or near the nucleus pulposus of an intervertebral disc etc.) to non-toxic components after or while a therapeutic agent has been or is being released. By "bioerosion" it is meant a process by which the implant or portion thereof will dissolve or erode or degrade over time due, at least in part, to contact with substances found in the surrounding tissue, fluids or by cellular action. By "bioresorbable" it is meant that the implant or portion thereof will be broken down and resorbed within the human body, for example, by a cell or tissue. "Biocompatible" means that the implant will not cause substantial cell damage or tissue irritation or necrosis at the target tissue site.

The phrases "sustained release" and "sustain release" (also referred to as extended release or controlled release) are used herein to refer to one or more therapeutic agent(s) that is introduced into the nucleus pulposus of the intervertebral disc of a human or other vertebrate and continuously or continually releases a stream of one or more therapeutic agents over a predetermined time period and at a therapeutic level sufficient to achieve a desired therapeutic effect throughout the predetermined time period.

The phrase "immediate release" is used herein to refer to one or more therapeutic agent(s) that is introduced into the nucleus pulposus of the intervertebral disc and that is allowed to dissolve in or become absorbed at the location to which it is administered, with no intention of delaying or prolonging the dissolution or absorption of the therapeutic agent.

The phrase "delayed release" is used herein to refer to one or more therapeutic agent(s) that is introduced into the nucleus pulposus of the intervertebral disc and that is allowed to dissolve in or become absorbed at the location to which it is administered, only after an outer layer is compromised or breached with the specific intention of delaying or prolonging the dissolution or absorption of the therapeutic agent, i.e. chemonucleolysis agent.

The term "inert" refers to one or more substances that have no therapeutic activity.

"Treating" or "treatment" of a disease or condition refers to executing a protocol that may include administering one or more drugs to a patient (human, normal or otherwise, or other vertebrate), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes protocols that have only a marginal effect on the patient. Treatment can include inhibiting the disease, e.g., arresting its development; or relieving the disease, e.g., causing regression of the disease. For example, treatment can include reducing acute or chronic inflammation, alleviating pain, and inducing re-growth of new disc and other tissues; as in an implant procedure designed to reduce inflammation and pain associated with inflammation of intervertebral discs.

Methods and devices for the localized delivery of active agents to an essentially intact intervertebral disc are provided. The disclosed methods of treatment do not require the surgical removal of disc tissues. The disclosed methods and devices can be used to treat various conditions of the intervertebral disc including, but not limited to, protrusion, herniation, discogenic pain, dehydration and degeneration. The implants incorporate one or more active agents in an inner layer that is encapsulated in an inert outer layer. By using the implants of the present invention, detrimental side effects typically associated with direct injection of an active agent in liquid form (including leakage and overdose), implantation of an immediate release active agent (including proteolytic degradation upon contact by chemonucleolysis agents) can be reduced or eliminated. Methods of incorporating one or more active agents into the inner layer of a compact implantable device are also provided.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure.

The implant devices of the present invention can be delivered into the nucleus pulposus of an intervertebral disc through a small opening or aperture in the annulus fibrosus. Once implanted, the implant is tracked to determine location and can be repositioned if implanted in the wrong location. Once the inert outer layer bioerodes over time, the inner layer can provide a controlled and/or sustained release or be released immediately after the outer layer is breached of one or more active agents from the implanted device to the surrounding disc tissues.

The implant can be of any size and shape suitable for implantation into the intervertebral disc space of a vertebrate. Preferably, the device is compact in cross-section for delivery to the disc space though a small opening or aperture. According to one embodiment of the invention, the device is an elongate solid body having an inner and an outer layer. The elongated body can, for example, be rod-shaped having a rounded or tapered insertion end. In the alternative, the shape of the implant can be spherical, oblong, torpedo shaped, or any shape that facilitates trouble-free insertion into to the area of treatment. The implant may comprise multiple units of same or different shapes; the units may be connected or not connected.

The proposed methods and implants of the present invention offer several advantages and can be used for various treatments of the intervertebral disc. Exemplary treatments include, but are not limited to, chemonucleolysis, pain-management, disc repair, disc regeneration, and reduction of inflammation.

According to one embodiment of the present invention, the cross section of the elongated solid body can have a maximum dimension of five (5) mm or less. According to further embodiments, the cross section of the elongated solid body has a maximum dimension of three (3) mm or less, two (2) mm or less, or one (1) mm or less. The phrase "maximum dimension" refers to the longest straight line that can be drawn on a given area. For example, the maximum dimension of a circle is its diameter. The cross-section of the device can be of any shape. For example, the cross section can be circular, elongated, torpedo shaped, spherical, oval or polygonal (e.g., octagonal). A tapered or rounded leading end can be used so as to require less force to insert through a small aperture than a square-leading end.

The shape and size of the implant can be chosen to achieve the desired release characteristics from the device. The thickness of each layer, as well as, the ratio of binder to active ingredient in the inner layer can be chosen to achieve the desired release rate. In making the implant of the present invention the particular binder and inert material used can also be chosen to achieve the desired release rate.

Figure 1A:
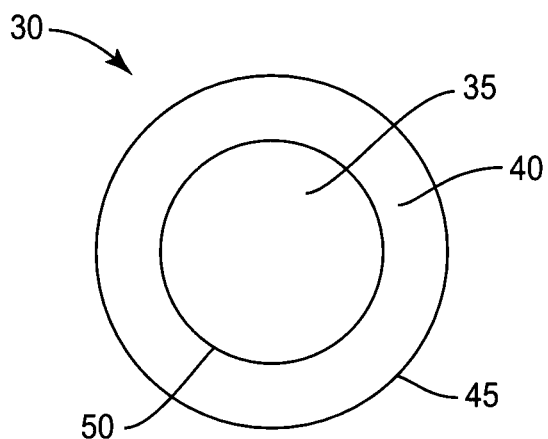
FIG. 1A shows a cross-section of a particular shape of the implant of the present invention.
Figure 1B:
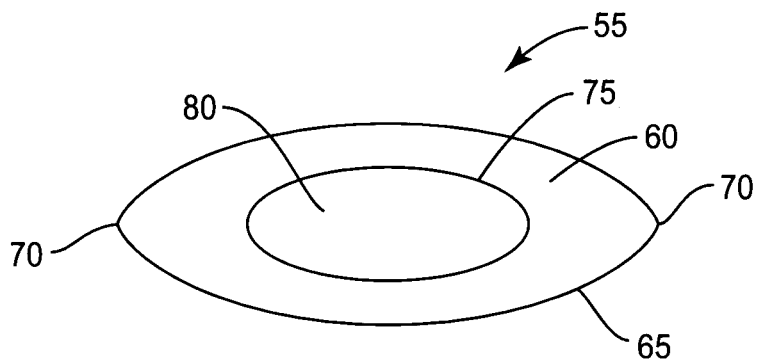
FIG. 1B shows a cross-section of yet another particular shape of the implant of the present invention.
Figure 3:
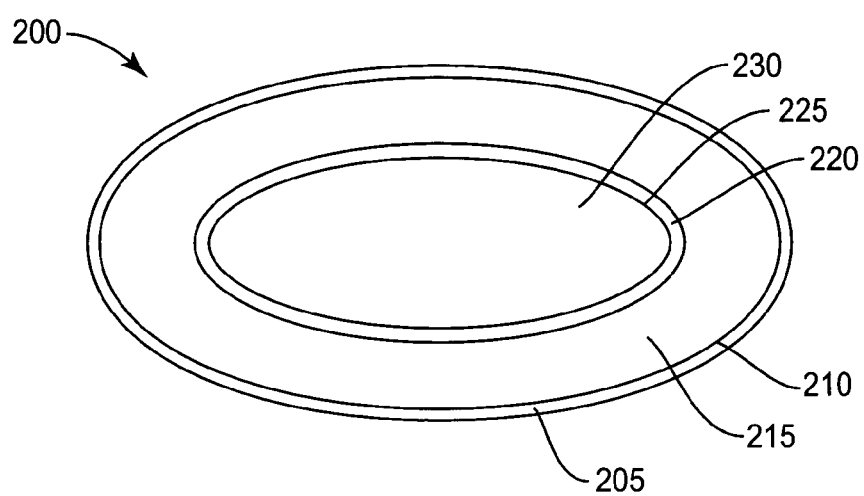
FIG. 3 shows a cross-section of an implant of the present invention having coated outer and inner surfaces.

FIG. 1 provides a cross-section of an elongated intervertebral disc implant 10 having an outer layer 20 configured to encapsulate an inner layer 15. The inner layer 15 comprises a mixture of active agents with or without a binder and the outer layer 20 is made from one or more inert materials. The elongated intervertebral disc implant 10 can have rounded ends so as to allow for easy implantation of the device. FIGS. 1A and 1B show alternative shapes for the intervertebral disc implants. In FIG. 1A the implant 30 is spherical in shape and has an outer layer 40 configured to encapsulate an inner layer 35. A transition line 50 separates the inner and outer layers of the implant. This transition line can consist of a coating on the inner layer 35 (as shown in FIG. 3) that maintains the active agents in the inner layer 35 until being dissolved. In the alternative, the transition line 50 is not a coating but instead is the interface where the inert outer layer 40 meets the inner layer 35.

The outer layer 40 has an outer surface 45 that can be marked with information and concentration of the active agents in the inner layer 35. The outer surface 45 can also be marked with information concerning the rate of release of the active agents. As with FIG. 1, the inner layer 35 can comprise a mixture of active agents and binders and the outer layer 40 is made from one or more inert materials. FIG. 1B shows yet another possible shape for the intervertebral disc implant of the present invention. The basic structure is the similar to the implant shown in FIGS. 1 and 1A except the ends 70 are pointed in shape in order to facilitate implantation of the device. The implant 55 of FIG. 1B has an inner layer 80 and an outer layer 60 that is separated by a transition layer 75 having the same properties as described in FIGS. 1 and 1A.

Figure 2:
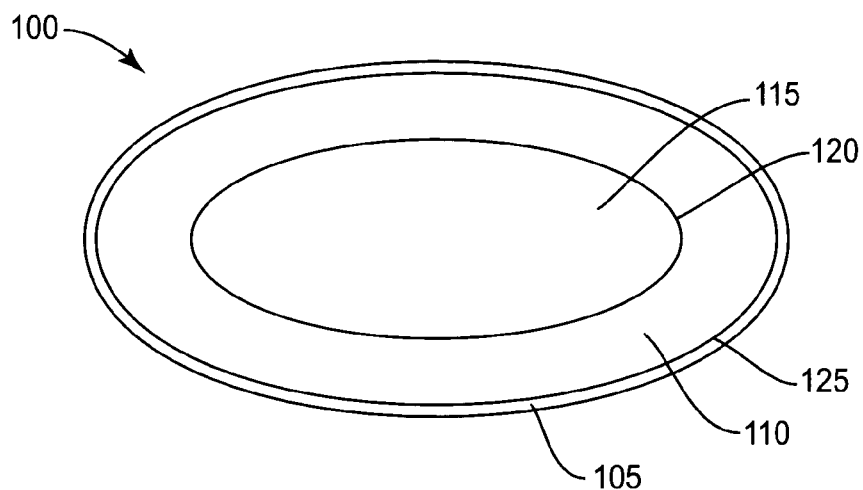
FIG. 2 shows a cross-section of a coated implant of the present invention.

FIG. 2 illustrates a cross-section of an elongated intervertebral disc implant 100 having an outer layer 110 configured to encapsulate an inner layer 115 separated by a transition line 120 that separates the inner layer 115 from the outer layer 110. This transition line can be a coating on the inner layer 115 surface that maintains the active agents in the inner layer 115 until being bioeroded. In the alternative, the transition line 120 is simply where the inert outer layer 110 meets the inner layer 115 and the active ingredient is released when the inert outer layer 110 is dissolved. As shown in FIG. 2, the outer layer 110 has a coating 105 on the outer surface 125 of the outer layer 110 that can have indicia and/or dosing information, as well as, indicia indicating the specific agents in the inner layer 115.

The outer coating 105 may also have radio-opaque and/or x-ray markers that can be used to track the location of the implant once placed into the desired area. The outer coating 105 further delays the release of the active agents from the inner layer since this coating, as well as the inert outer layer, has to dissolve or degrade in order for the active agents of the inner layer 115 to be released. In essence, this coating provides additional time for the surgeon to locate the implant, access whether the implant is in the desired location and or if not, to reposition it to the desired location before any active agents are released. The coating is an additional barrier to the release of the active ingredient from the inner layer.

FIG. 3 shows yet another embodiment of the present invention wherein both the outer surface of the outer layer and the outer surface of the inner layer are coated. This implant would provide yet an additional barrier to release of therapeutic agents from the inner layer. This can be used in situations where additional time is necessary to determine if the location of the implant is correct.

FIG. 3 shows an implant 200 having a coating 205 on the outer surface 210. The outer surface 225 of the inner layer 230 that separates the outer layer 215 from the inner layer 230 is also coated 220. This coating, like the coating 205 on outer layer 215, must be dissolved in order to release the therapeutic agent. Thus, this second coating further delays the degradation of the inner layer and thus, the release the therapeutic agent.

The implant 200 can be made by forming the inner layer 230 by combining at least one therapeutic agent with binders under pressure and then coated with coating 220. Once coated, the outer layer 215 can be disposed on the coated inner layer to produce the uncoated implant. The outer coating 205 can then be disposed on the outer layer to produce the double-coated implant 200. Other methods can be used to produce the implants shown in FIG. 3.

Examples of active agents which can be incorporated into the devices include, but are not limited to: chemonucleolysis agents such as chymopapain, collagenase, chondroitinase-ABC, hyaluronidase, human proteolytic enzymes, and poly-cationic substances; pain medications such as codeine, propoxyphene, hydrocodone, and oxycodone; anti-inflammatory agents; antibacterial agents; cells; nucleic acid derivatives; and growth factors such as transforming growth factor, proteins, bone morphogenetic proteins, fibroblast growth factors, platelet-derived growth factors, and insulin-like growth factors. Any of the aforementioned active agents or combinations thereof can be incorporated into the inner layer of the device.

Examples of anti-inflammatory agents include, but are not limited to, a statin, sulindac, sulfasalazine, naroxyn, diclofenac, indomethacin, ibuprofen, flurbiprofen, ketoprofen, aclofenac, aloxiprin, aproxen, aspirin, diflunisal, fenoprofen, mefenamic acid, naproxen, phenylbutazone, piroxicam, meloxicam, salicylamide, salicylic acid, desoxysulindac, tenoxicam, ketoralac, clonidine, flufenisal, salsalate, triethanolamine salicylate, aminopyrine, antipyrine, oxyphenbutazone, apazone, cintazone, flufenamic acid, clonixeril, clonixin, meclofenamic acid, flunixin, colchicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, triflumidate, fenamates (mefenamic acid, meclofenamic acid), nabumetone, celecoxib, etodolac, nimesulide, apazone, gold, tepoxalin; dithiocarbamate, or a combination thereof. Anti-inflammatory agents also include other compounds such as steroids, such as for example, fluocinolone, cortisol, cortisone, hydrocortisone, fludrocortisone, prednisone, prednisolone, methylprednisolone, triamcinolone, betamethasone, dexamethasone, beclomethasone, fluticasone interleukin-1 receptor antagonists, thalidomide (a TNF-α release inhibitor), thalidomide analogues (which reduce TNF-α production by macrophages), bone morphogenetic protein (BMP) type 2 or BMP-4 (inhibitors of caspase 8, a TNF-α activator), quinapril (an inhibitor of angiotensin II, which upregulates TNF-α), interferons such as IL-11 (which modulate TNF-α receptor expression), and aurin-tricarboxylic acid (which inhibits TNF-α), guanidinoethyldisulfide, or a combination thereof.

Examples of binders or matrix materials include, but are not limited to: non-resorbable polymers such as poly(urethanes), poly(siloxanes}, poly(methyl methacrylate), poly (ethylene), poly(vinyl alcohol, poly(vinyl pyrrolidon), poly (2-hydroxy ethyl methacrylate), poly(acrylic acid), poly (ethylene-co-vinyl acetate, poly(ethylene glycol), poly (methacrylic acid), and polyacrylamide; bioresorbable polymers such as polylactides (PLA), polyglycolides (PGA), poly(lactide-co-glycolides) (PLGA), polyanhydrides, and polyorthoesters; and natural polymers such as: polysaccharides, collagens, silk, elastin, keratin, albumin, and fibrin. Any combination of the above binders can be used alone or in combination to produce the inert outer layer and alone or in combination together with one or more of the active agents listed above to produce the inner layer of the device.

When a growth factor is included in the inner layer of the device, various types of cells can be injected into the disc space when the growth factor is released from the inner layer of the device in order to promote disc repair and regeneration. Exemplary cells that can be released into the intervertebral disc during the from the inner layer in implants having growth factors in the inner layer of the device include, but are not limited to, notochordal cells, fibrochrondrocytes, and mesenchymal stem cells. The cells can be modified with a growth factor. For example, the cells can be transfected with a nucleic acid (e.g., an expression vector) encoding a growth factor such as a bone morphogenetic protein or a LIM mineralization protein.

As set forth above, the inner layer of the intervertebral disc implant can be formed by consolidating an admixture comprising a binder and one or more active agents into a solid body. Alternatively, the inner layer of the intervertebral disc implant can include a plurality of particles at least some of which comprise an active agent wherein the particles are unconsolidated (i.e., in loose admixture). The inner layer of the implant can further include particles comprising a binder. The particles comprising a binder can be mixed with the particles comprising the active agent in the inner layer in order to facilitate handling and delivery of the particulate material into the disc nucleus.

The inner layer of the device can be made by mixing together particles of the active agent and the binder, forming a consolidated solid body from the admixture (e.g., using heat and/or pressure), and comminuting the solid body to form particles of the desired size. The inner layer could also be made so that at least some of the particles comprise a first active agent and at least some of the particles comprise a second active agent. Alternatively, an admixture of first and second active agents and binder can be consolidated into a solid body and comminuted into particles to form the implant. According to this embodiment, individual particles in the implant comprise the first and second active agents as well as the binder. Implants comprising additional active agents (i.e., three or more) can also be made using the techniques described above.

For either the solid body (e.g., consolidated) implants or the particulate (e.g., non-consolidated) implants, the particles comprising active agent(s) in the inner layer of the implant can be sized to achieve a desired release profile. Smaller particles have a higher surface area and will therefore typically result in more rapid release of the active agent. According to one embodiment, the particles of active agent(s) in the inner layer of the implant can have an average diameter of about 0.1 to about 500 μm. In other embodiments of the present invention, the particles of active agent in the inner layer of the implant can have an average diameter of from about 0.5 to about 250 μm or from 1 to about 100 μm. When the inner layer of the implant is a solid body comprising different active agents, active agents having different particle sizes can be used to achieve the desired release characteristics for that active agent once the outer layer and any coating on the inner layer bioerodes.

The amount of binder used to make the inner and outer layers of the implant can also be varied to achieve the desired break down of the outer layer and the release characteristics of the active agent(s) from the inner layer of the implant once the outer layer dissolves. According to one exemplary embodiment of the present invention, the inner layer of the implant of the present invention can comprise from about 10 to about 100% by volume of the active agent with the remainder (i.e., 0 to about 90% by volume) being binder. According to further exemplary embodiments, the implant can comprise from about 25 to about 75% by volume of the active agent with the remainder (i.e., about 25 to about 75% by volume) being binder. In another exemplary embodiment of the present invention, the inner layer is a gel, hydrogel, emulsion, suspension or liquid having one or more active agents incorporated therein. Different amounts of binder used, as well as, whether particles, liquid, gels etc. are used can be varied in order to achieve the desired release characteristics for that active agent.

Suitable gel polymers that may be used in the outer and/or inner layers of the implant of the present invention may be soluble in an organic solvent. The solubility of a polymer in a solvent varies depending on the crystallinity, hydrophobicity, hydrogen bonding and molecular weight of the polymer. Lower molecular weight polymers will normally dissolve more readily in an organic solvent than high-molecular weight polymers. A polymeric gel that includes a high molecular weight polymer tends to coagulate or solidify more quickly than a polymeric composition that includes a low-molecular weight polymer. Polymeric gel formulations that include high molecular weight polymers, also tend to have a higher solution viscosity than a polymeric gel that includes low-molecular weight polymers. In various embodiments, the molecular weight of the polymer can be a wide range of values. The average molecular weight of the polymer can be from about 1000 to about 10,000,000; or about 1,000 to about 1,000,000; or about 5,000 to about 500,000; or about 10,000 to about 100,000; or about 20,000 to 50,000.

In various embodiments of the present invention, the gel used to produce the inert outer layer and/or the active inner layer has an inherent viscosity (abbreviated as "I.V." and units are in deciliters/gram), which is a measure of the gel's molecular weight and degradation time (e.g., a gel with a high inherent viscosity has a higher molecular weight and longer degradation time). Typically, a gel with a high molecular weight provides a more solid compacted implant layer and the layer takes more time to degrade. In contrast, a gel with a low molecular weight degrades more quickly and provides a softer layer. In various embodiments, the gel has a molecular weight, as shown by the inherent viscosity, from about 0.10 dL/g to about 1.2 dLg or from about 0.10 dL/g to about 0.40 dL/g. Other IV ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.50 dL/g, about 0.50 to about 0.70 dL/g, about 0.60 to about 0.80 dL/g, about 0.70 to about 0.90 dL/g, and about 0.80 to about 1.00 dL/g.

A gel used in the present invention may optionally have a viscosity enhancing agent such as, for example, hydroxypropyl cellulose, hydroxypropyl methylcellulose, hydroxyethyl methylcellulose, carboxymethylcellulose and salts thereof, Carbopol, poly-(hydroxyethylmethacrylate), poly-(methoxyethylmethacrylate), poly(methoxyethoxyethyl methacrylate), polymethylmethacrylate (PMMA), methylmethacrylate (MMA), gelatin, polyvinyl alcohols, propylene glycol, mPEG, PEG 200, PEG 300, PEG 400, PEG 500, PEG 600, PEG 700, PEG 800, PEG 900, PEG 1000, PEG 1450, PEG 3350, PEG 4500, PEG 8000 or combinations thereof.

Hydrogels obtained from natural sources are particularly appealing because they are more likely to be biodegradable and biocompatible for in vivo applications. Suitable hydrogels include natural hydrogels, such as for example, gelatin, collagen, silk, elastin, fibrin and polysaccharide-derived polymers like agarose, and chitosan, glucomannan gel, hyaluronic acid, polysaccharides, such as cross-linked carboxyl-containing polysaccharides, or a combination thereof. Synthetic hydrogels include, but are not limited to those formed from polyvinyl alcohol, acrylamides such as polyacrylic acid and poly (acrylonitrile-acrylic acid), polyurethanes, polyethylene glycol (e.g., PEG 3350, PEG 4500, PEG 8000), silicone, polyolefins such as polyisobutylene and polyisoprene, copolymers of silicone and polyurethane, neoprene, nitrile, vulcanized rubber, poly(N-vinyl-2-pyrrolidone), acrylates such as poly(2-hydroxy ethyl methacrylate) and copolymers of acrylates with N-vinyl pyrolidone, N-vinyl lactams, polyacrylonitrile or combinations thereof. The hydrogel materials may further be cross-linked to provide further strength as needed. Examples of different types of polyurethanes include thermoplastic or thermoset polyurethanes, aliphatic or aromatic polyurethanes, polyetherurethane, polycarbonate-urethane or silicone polyether-urethane, or a combination thereof.

In various embodiments of the present invention, in the inner layer rather than directly admixing the therapeutic agent into the gel, microspheres may be dispersed within the gel, the microspheres being loaded with the therapeutic agent. For example, an implant may have at least one chemonucleolysis agent suspended in the gel that may be deployed around the implant site upon dissolving of the inert outer layer. Dispersed within the gel may be a plurality of microspheres that encapsulate the desired therapeutic agent. Certain of these microspheres degrade once released from the gel, after the inert outer layer is dissolved thus releasing the therapeutic agent, ie. at least one chemonucleolysis agent Microspheres, much like a fluid, may disperse relatively quickly, depending upon the surrounding tissue type, and hence disperse the therapeutic agent. In some situations, this may be desirable; in others, it may be more desirable to keep the therapeutic agent tightly constrained to a well-defined target site. The present invention also contemplates the use of adherent gels to so constrain dispersal of the therapeutic agent. These gels may be deployed, for example, once the inert outer layer is compromised in the tissue surrounding the implant.

Once formed, the implant can be implanted into an intervertebral disc using a hollow tube (e.g., a trocar) as a delivery device. Accordingly, the present invention is also directed to a method of treating at least one condition of an intervertebral disc in a patient in need of such treatment and tracking the implant to assure that it is in the desired location before the active agent is allowed to enter the surrounding tissue. The method comprises the following steps starting with the placement of at least one of the intervertebral disc implants of the present invention into an intervertebral space of a patient. Once placed, the location of the intervertebral disc implant is determined by tracking the location of the radio opaque x-ray markers using either x-ray imaging or other detection means. It is determined whether the location of the implant is correct, and if it is not correct, the implant is moved from its location and inserted into the intervertebral space of the patient at a location different from which the implant was removed. It is determined once again whether the location of the implant is correct; if not, the repositioning procedure is performed again. Once in the desired location, the implant is allowed to bioerode and release the chemonucleolysis agent in the inner layer of the implant into surroundings once the outer layer and, if present, coating(s) dissolve or degrade and the inner layer is exposed to the tissue. Once released, the agent is allowed to act on the surrounding tissue.

Implantation of the implant of the present invention can be achieved by inserting a needle/trocar assembly into the intervertebral space such that the inserted end of the trocar is inside the nucleus pulposus of an intervertebral disc. Once in place the needle is removed and at least one implant described herein is placed into the trocar for placement into the intervertebral space. Once the implant is in the trocar it is pushed into the nucleus pulposus of the intervertebral disc and the location of the implant is detected using the steps discussed above. Once in the desired location, the trocar is removed and the procedure is finalized. The implant will then be monitored by the surgeon for its effectiveness in treating the intervertebral disc disorder.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An intervertebral disc implant comprising
an inner layer comprising at least one chemonucleolysis agent; and
an inert outer layer disposed about the inner layer so as to fully encapsulate said inner layer,
wherein said implant is configured so that release of said chemonucleolysis agent into tissue surrounding said implant is delayed until said inert outer layer bioerodes.

2. The intervertebral disc implant of claim 1, wherein the inert outer layer includes a plurality of binder particles.

3. The intervertebral disc implant of claim 2, wherein said plurality of binder particles of said inert outer layer degrades at different rates in order to prevent the release of said at least one chemonucleolysis agent from said inner layer for a predetermined amount of time.

4. The intervertebral disc implant of claim 1 further comprising a coating disposed on an outermost surface of said outer layer wherein said coating must dissolve or degrade prior to the dissolution or degradation of said inert outer layer thereby slowing down the rate of release of said at least one chemonucleolysis agent from said inner layer.

5. The intervertebral disc implant of claim 1, further comprising at least one therapeutic agent selected from the group consisting of anti-inflammatory agents, pain medication, growth factors, anti-bacterial agents and combinations thereof.

6. The intervertebral disc implant of claim 1, wherein said inner layer includes a plurality of particles and wherein at least some of the particles comprise said at least one chemonucleolysis agent.

7. The intervertebral disc implant of claim 6, wherein the particles comprising said at least one chemonucleolysis agent have an average diameter of about 0.5 to about 250 µm.

8. The intervertebral disc implant of claim 1, wherein said at least one chemonucleolysis agent is selected from the group consisting of chymopapain, collagenase, chondroitinase-ABC, hyaluronidase, human proteolytic enzymes, and polycationic substances.

9. The intervertebral disc implant of claim 5, wherein said inner layer includes a plurality of particles and wherein at least some of the particles comprise said at least one therapeutic agent.

10. The intervertebral disc implant of claim 1, wherein said inner layer is a liquid, gel, hydrogel, emulsion, particulate or solid.

11. The intervertebral disc implant of claim 1, further comprising a marker for tracking the location of said intervertebral disc implant when placed into the nucleus pulposus of an intervertebral disc.

12. The intervertebral disc implant of claim 11, wherein said marker is an x-ray marker or radio-opaque marker.

13. The intervertebral disc implant of claim 5, wherein said pain medication is selected from the group consisting of codeine, propoxyphene, hydrocodone, oxycodone and combinations thereof.

14. The intervertebral disc implant of claim 5, wherein said growth factor is selected from the group consisting of a transforming growth factor-beta protein, a bone morphogenetic protein, a fibroblast growth factor, a platelet-derived growth factor, an insulin-like growth factor and combinations thereof.

15. The intervertebral disc implant of claim 12, wherein said x-ray marker comprises barium sulfate, platinum or tantalum.

16. A method for treating at least one condition of an intervertebral disc in a patient in need of such treatment, said method comprising: placing said intervertebral disc implant of claim 1 into the nucleus pulposus of an intervertebral space of said patient, wherein said placing releases said chemonucleolysis agent into the nucleus pulposus surrounding the implant after said inert outer layer bioerodes, thereby proteolytically degrading the nucleus pulposus.

17. The method of claim 16, wherein the placing of said implant into the intervertebral space comprises:

inserting a needle/trocar assembly into the intervertebral space such that the inserted end of the trocar is inside the nucleus pulposus of an intervertebral disc;

removing said needle;

placing said implant into said trocar;

pushing said implant into the nucleus pulposus of the intervertebral disc; and removing the trocar.

18. A method for treating at least one condition of an intervertebral disc in a patient in need of such treatment and tracking said implant for proper placement, said method comprising:
(a) placing said intervertebral disc implant of claim 11 into an intervertebral space of said patient,
(b) determining the position of said intervertebral disc implant by detecting a location of said x-ray marker or radio-opaque marker using an imaging device and determining whether said location of said implant is correct, if said implant is not in the correct location proceeding to step (c) and if said implant is in the correct location proceeding to step (d);
(c) removing said implant from said intervertebral disc and reinserting said implant in a different location in said intervertebral disc from which said implant was removed and repeating step (b); and
(d) allowing said outer layer of said implant to bioerode and release said chemonucleolysis agent in said inner layer to the nucleus pulposus surrounding said implant, thereby treating said condition of said patient.

19. The method of claim 18, wherein the placing of said implant into the intervertebral space of step (a) comprises
inserting a needle/trocar assembly into the intervertebral space such that the inserted end of the trocar is inside the nucleus pulposus of an intervertebral disc;
removing said needle;
placing said implant into said trocar;
pushing said implant into the nucleus pulposus of the intervertebral disc and determining the position of said intervertebral disc implant by detecting the position according to step (b); and
removing the trocar upon the completion of step (d).

20. The method of claim 18 wherein said implant further comprises at least one therapeutic agent selected from the group consisting of anti-inflammatory agents, pain medication, growth factors, anti-bacterial agents and combinations thereof.

21. The intervertebral disc implant of claim 1, wherein said inner layer comprises a hydrogel.

* * * * *